(12) United States Patent
Spottiswoode et al.

(10) Patent No.: US 10,736,596 B2
(45) Date of Patent: Aug. 11, 2020

(54) SYSTEM TO IMPROVE NUCLEAR IMAGE OF MOVING VOLUME

(71) Applicant: Siemens Medical Solutions USA, Inc., Malvern, PA (US)

(72) Inventors: Bruce S. Spottiswoode, Knoxville, TN (US); Juergen Soldner, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 166 days.

(21) Appl. No.: 16/021,264

(22) Filed: Jun. 28, 2018

(65) Prior Publication Data

US 2020/0000424 A1    Jan. 2, 2020

(51) Int. Cl.
| | |
|---|---|
| *A61B 6/00* | (2006.01) |
| *A61B 6/03* | (2006.01) |
| *G01T 1/164* | (2006.01) |
| *G01T 1/29* | (2006.01) |

(52) U.S. Cl.
CPC ............ *A61B 6/5264* (2013.01); *A61B 6/037* (2013.01); *A61B 6/5235* (2013.01); *G01T 1/1642* (2013.01); *G01T 1/2985* (2013.01)

(58) Field of Classification Search
None
See application file for complete search history.

(56) References Cited

U.S. PATENT DOCUMENTS

| | | | |
|---|---|---|---|
| 6,236,706 B1 * | 5/2001 | Hsieh | A61B 6/032 378/15 |
| 2009/0118609 A1 * | 5/2009 | Rahn | A61B 6/12 600/411 |
| 2009/0253980 A1 | 10/2009 | Wollenweber et al. | |
| 2015/0289832 A1 * | 10/2015 | Bal | A61B 6/5264 600/411 |

OTHER PUBLICATIONS

Kovács, Balázs, "List Mode PET reconstruction", Sixth Hungarian Conference on Computer Graphics and Geometry, Budapest 2012, 6 pp.
Sadek A Nehmeh et al: "Deep-Inspiration Breath-Hold PET/CT of the Thorax", The Journal of Nuclear Medicine, Jan. 1, 2007 (Jan. 1, 2007), pp. 22-26.

(Continued)

*Primary Examiner* — Edwin C Gunberg

(57) ABSTRACT

A system and method include execution of a first nuclear imaging scan to acquire first nuclear imaging scan data of a body; generation of a target image based on the first nuclear imaging scan data execute a second nuclear imaging scan to acquire second nuclear imaging scan data of the body association of each of a plurality of portions of the second nuclear imaging scan data with a respective one of a plurality of motion phases of the body, generation, for each of the plurality of motion phases of the body, of a binned image based on the portion of the second nuclear imaging scan data associated with the motion phase, performance of motion-correction on each of the plurality of binned images based on the target image to generate a plurality of motion-corrected binned images, and generation of an image based on the target image and the plurality of motion-corrected binned images.

20 Claims, 6 Drawing Sheets

(56) References Cited

OTHER PUBLICATIONS

Nehmeh S A et al: "Respiratory Motion in Positron Emission Tomography/Computed Tomography: A Review", Seminars in Nuclear Medicine, Elsevier, Amsterdam, NL, vol. 38, No. 3, May 1, 2008 (May 1, 2008), pp. 167-176.
Paul B Shyn et al: "Minimizing Image Misregistration during PET/CT guided Percutaneous Interventions with Monitored Breathhold PET and CT Acquisitions", Journal of Vascular and Interventional Radiology, Elsevier, Amsterdam, NL, vol. 22, No. 9, Jun. 22, 2011 (Jun. 22, 2011), pp. 1287-1292.

\* cited by examiner

SYSTEM TO IMPROVE NUCLEAR IMAGE OF MOVING VOLUME

BACKGROUND

According to conventional nuclear imaging, a radiopharmaceutical is introduced into a patient body by injection or ingestion. The radiopharmaceutical emits gamma rays (in the case of single-photon-emission-computer-tomography (SPECT) imaging) or positrons which annihilate with electrons to produce gamma rays (in the case of positron-emission-tomography (PET) imaging). A detector system located outside the body detects the emitted gamma rays and reconstructs images based thereon.

The duration for which a detector system is exposed to a body portion is directly related to the number of gamma rays detected from the body portion and, as a result, to the quality of the image reconstructed therefrom. However, the longer the duration, the more likely that the body portion will move, thereby blurring the resulting image. Imaging the abdominal, thoracic and cardiac areas is particularly problematic, since these areas move almost continuously due to natural physiological processes.

To address body movement during imaging, some conventional nuclear imaging processes require a patient to hold her breath while scanning the thoracic area, for example. The duration for which the (typically sick) patient is able to hold her breath is usually too short for detecting a sufficient number of gamma rays to form a suitable image. The number of detected gamma rays may be increased by scanning the area successively over a series of breath-holds, but this process is quite taxing to the patient and may result in artifacts due to registration errors between the successive images. What is needed are systems to generate nuclear images of moving volumes having improved image resolution and reduced motion artifacts.

DETAILED DESCRIPTION

The following description is provided to enable any person in the art to make and use the described embodiments and sets forth the best mode contemplated for carrying out the described embodiments. Various modifications, however, will remain apparent to those in the art.

Generally, some embodiments execute a rapid nuclear imaging scan while a patient is in a breath-hold position, followed by a standard nuclear imaging scan while the patient is breathing normally. The data of the standard scan is binned according to the patient's phase of motion at the time of data detection. The binned data is used to reconstruct respective binned images, and each of the binned images is deformed to a target image generated from the rapid nuclear imaging scan. A higher-resolution composite image may then be efficiently created based on the deformed binned images and the target image, including all the data of the rapid nuclear imaging scan and the standard nuclear imaging scan, and minimizing artifacts caused by patient motion during the standard nuclear imaging scan.

According to some embodiments, a computed tomography image of the patient is acquired in the breath-hold position, temporally adjacent to execution of the rapid nuclear imaging scan. This computed tomography image may be aligned with the target image and therefore also with the higher-resolution composite image. Accordingly, the computed tomography image may be used to perform attenuation correction on the composite image, for example by generating an attenuation coefficient map based on the computed tomography image and applying the attenuation coefficient map to the composite image. Embodiments may therefore provide efficient generation of high-resolution and attenuation-corrected nuclear images of moving volumes.

Figure 1:
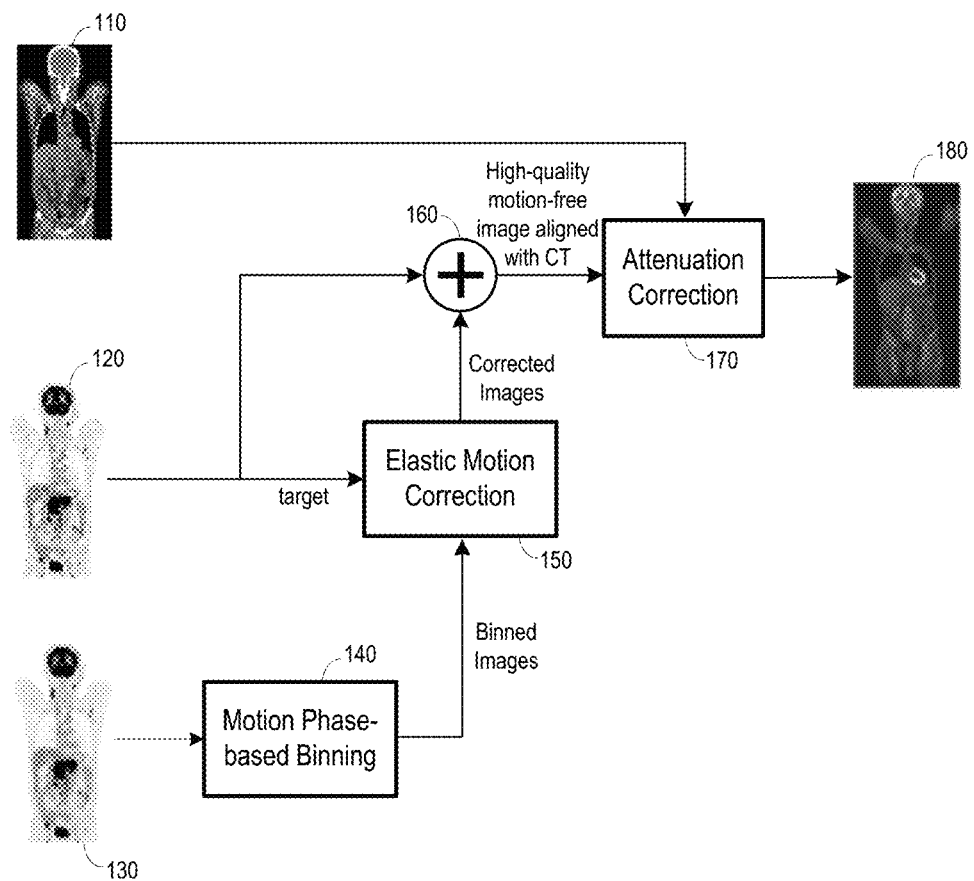
FIG. 1 is a block diagram of a system to generate an attenuation-corrected nuclear imaging image according to some embodiments.
Figure 2:
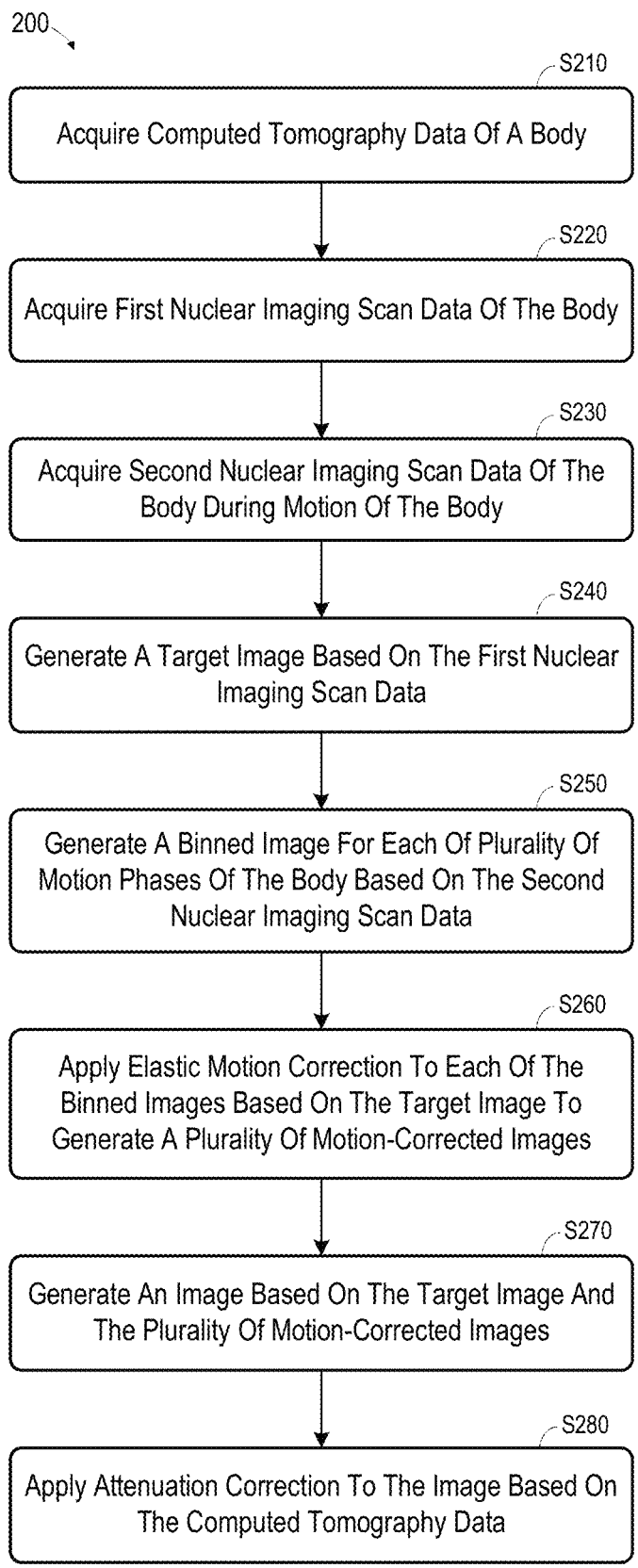
FIG. 2 is a flow diagram of a process to generate an attenuation-corrected nuclear imaging image according to some embodiments.

FIG. 1 illustrates an image generation process according to some embodiments. The process will be described with respect to flow diagram 200 of FIG. 2. Flow diagram 200 and other flows described herein may be executed using any suitable combination of hardware and software. Software program code embodying these processes may be stored by any non-transitory tangible medium, including a fixed disk, a volatile or non-volatile random-access memory, a floppy disk, a CD, a DVD, a Flash drive, or a magnetic tape. Embodiments are not limited to the examples described below.

Initially, computed tomography (CT) data 110 of a body is acquired at S210 as is known in the art. CT data 110 may be acquired by a CT scanner while the body is positioned within the CT scanner. Data 110 is represented in FIG. 1 as a slice of volumetric CT data, which is reconstructed based on many sets of two-dimensional CT image data acquired by the CT scanner at S210 as is known in the art.

Figure 3:
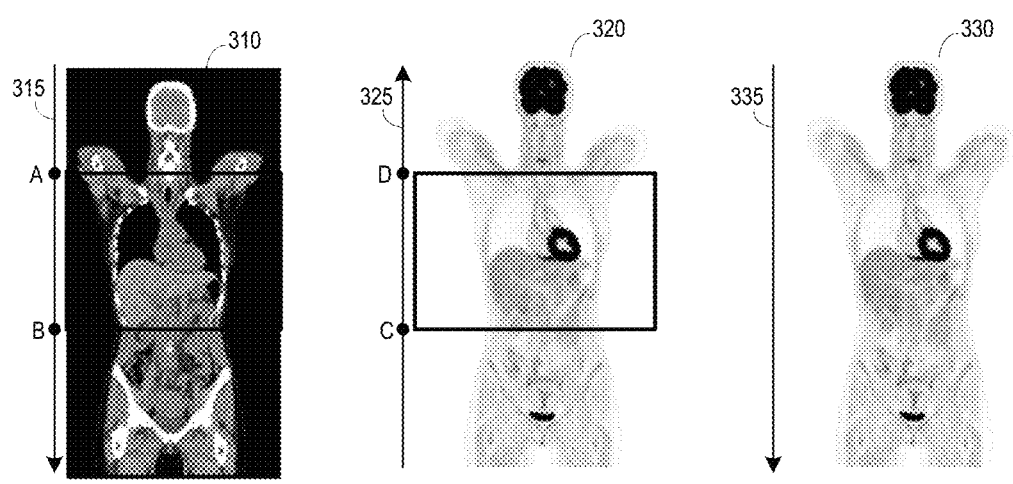
FIG. 3 illustrates acquisition of computed tomography data, first nuclear imaging data and second nuclear imaging data according to some embodiments.

According to some embodiments, at least a portion of CT data 110 is acquired while the body is in a breath-hold position. FIG. 3 illustrates CT data 310 acquired by scanning the body longitudinally in the direction indicated by arrow 315 at S210. Upon reaching position A, the patient is instructed to hold her breath. The breath is held until the scan reaches position B, at which point the patient is instructed to begin breathing normally. Since patient motion due to respiration occurs primarily in the region between positions A and B, the breath-hold process reduces motion artifacts that may otherwise be present in the CT image reconstructed from the acquired scan data. Also, due to the short duration of a typical CT scan, the patient is usually able to hold her breath for the required amount of time.

Returning to FIG. 2, first nuclear imaging scan data of the body is acquired at S220. Acquisition of the first nuclear imaging scan data is preceded by introduction of a suitable radiopharmaceutical in any suitable manner, as is known in the art. The present example will be described in the context of a PET system, but the data may be acquired by a SPECT system, a PET system, or another type of nuclear imaging system that is or becomes known.

PET data 120 of FIG. 1 represents the first nuclear imaging scan data acquired at S220, and is illustrated as a PET image. In some embodiments, PET data 120 may comprise a "PET scout", which was acquired at a higher scanning speed than a typical nuclear imaging scan. The higher scanning speed may result in a lower signal-to-noise ratio within PET data 120 than would be achieved at lower scanning speeds, due to the reduced time over which gamma rays are detected.

The higher scanning speed may also facilitate a breath-hold acquisition as described above with respect to S210. FIG. 3 shows PET data 320 acquired by scanning the body longitudinally in the direction indicated by arrow 325 at S220. Upon reaching position C, the patient is instructed to hold her breath. The breath is held until the scan reaches position D, at which point the patient is instructed to exhale and begin breathing normally. Again, because of the short duration of the scan at S220 (as compared to a typical nuclear imaging scan), the patient should be able to maintain the breath-hold position as the scan progresses from point C to point D. Accordingly, the patient is in the breath-hold position during scanning of the same body portion which was scanned in the breath-hold position at S210. Both the CT data and the PET data should therefore represent the body portion in a substantially-similar position.

The first nuclear imaging scan data may be acquired substantially contemporaneously with the acquisition of the CT data. For example, a CT imaging system of a PET/CT scanner may be operated to acquire the CT data at S210 while a patient lies in a given position on a bed of the PET/CT scanner, and a PET imaging system of the PET/CT scanner may be operated immediately thereafter to acquire the first nuclear imaging scan data at S220 while the patient remains on the bed in the given position. Because the geometric transformation (if any) between coordinates of the CT scanner and the PET scanner is known, the CT data and the PET data may be considered as substantially registered with one another.

Second nuclear imaging scan data is acquired at S230. The second nuclear imaging scan data is acquired during motion of the body. For example, the second nuclear imaging scan data may be acquired while the patient is breathing freely. Returning to FIG. 3, second nuclear imaging scan data 330 may be acquired by performing a conventional PET scan in the direction of arrow 335, without any restrictions on patient breathing. The second nuclear imaging scan data may be acquired at a slower scanning rate than the first nuclear imaging scan data acquired at S220. Accordingly, the second nuclear imaging scan data may represent more gamma-ray detections than the first nuclear imaging scan data, but an image reconstructed therefrom would include motion artifacts due to body motion during data acquisition.

A target image is generated based on the first nuclear imaging scan at S240. The target image may be generated by applying reconstruction algorithms to the first nuclear image scan data as is known in the art. PET data 120 of FIG. 1 illustrates such a target image, which exhibits a lower signal-to-noise ration than a typical PET image due to its shorter acquisition time.

Figure 4:
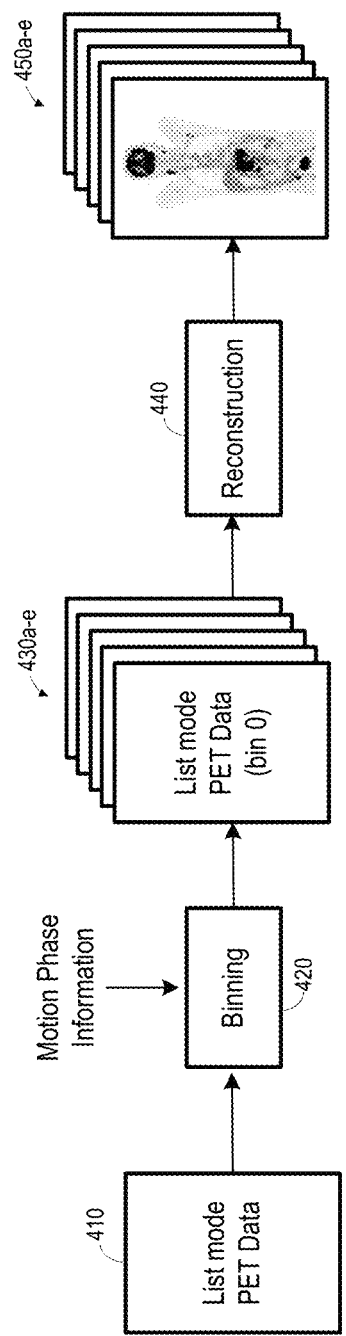
FIG. 4 is a block diagram illustrating generation of phase-associated images according to some embodiments.

Next, at S250, the second nuclear imaging scan data is used to generate a binned image for each of a plurality of motion phases of the body. FIG. 4 illustrates S250 according to some embodiments. In some embodiments, the second nuclear imaging scan data 410 is acquired in "list mode" in which each detected gamma-ray is associated with a detection time as well as other detected values which enable location of the emission event.

Binning component 420 receives list mode data 410 and motion phase information. The motion phase information may indicate the phases of motion in which the body resided at various times throughout acquisition of the list mode data. The motion phase information may be determined from the second nuclear imaging scan data itself or from a motion monitor which associates phases of motion with time. For example, a patient's respiratory cycle may be monitored and recorded during acquisition of the second nuclear imaging scan data using any respiratory monitoring system that is or becomes known.

Figure 5:
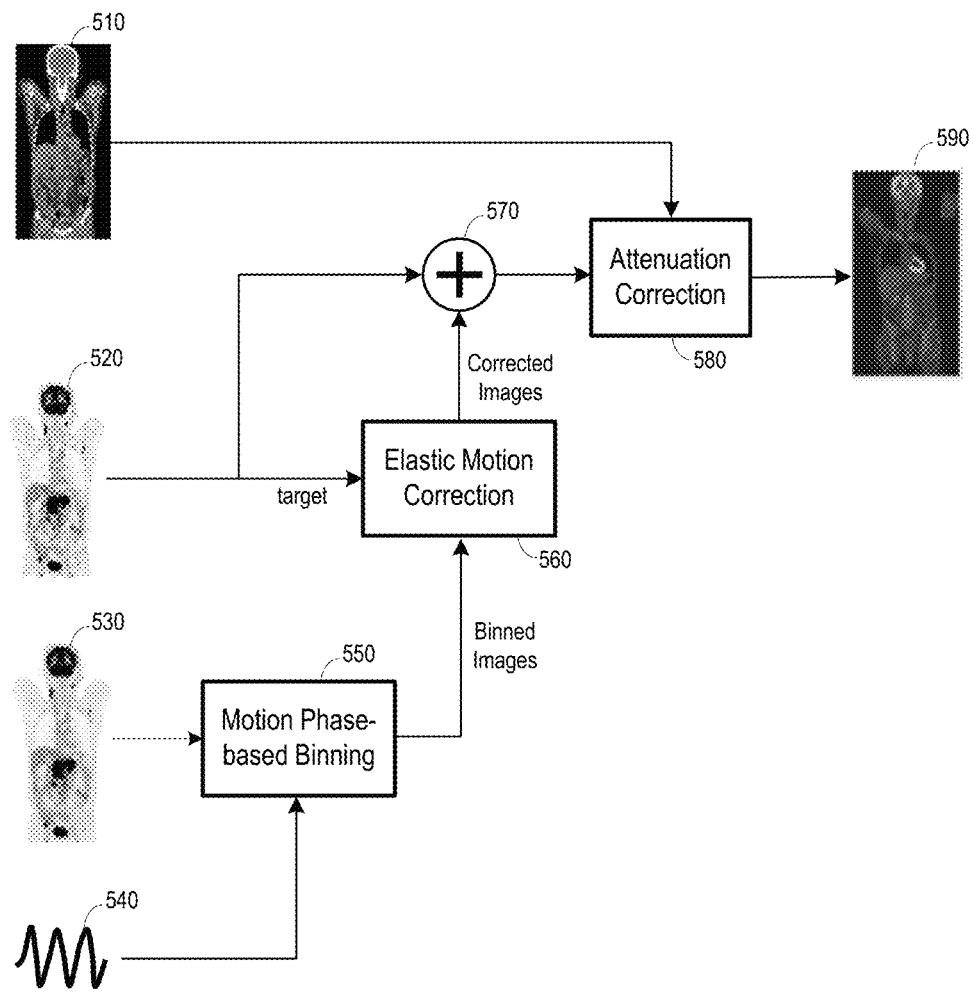
FIG. 5 is a block diagram of a system to generate an attenuation-corrected nuclear imaging image according to some embodiments.

FIG. 5 illustrates a system in which respiratory signal 540 is input to binning component 550 to assist with the binning process. Respiratory signal 540 may be acquired and transmitted by a respiratory monitor attached to the patient during acquisition of the second nuclear imaging scan data 530. The respiratory cycle may be divided into multiple phases, and the patient may experience several respiratory cycles during data acquisition. Using the list mode data and respiratory signal 540, binning component 550 (and/or 420) may associate each gamma-ray detection with the phase of the respiratory cycle during which the detection occurred.

Binned data 430a-e represents scan data separated into five bins, each of which represents a phase of motion. Embodiments are not limited to any particular number of bins/phases. The data of each bin represents gamma-ray detections which occurred during the phase of motion associated with the bin. Reconstruction component 440 generates an image based on each of binned data 430a-e, resulting in binned images 450a-e. Each of binned images 450a-e therefore represents the body as positioned during a phase of motion associated with a particular bin.

At S260, elastic motion correction is applied to each of the binned images based on to generate, for each binned image, a motion-corrected image. The elastic motion correction is executed to deform each binned image to the target image. FIG. 1 illustrates elastic motion correction component 150 receiving the binned images and the target image, and outputting corrected images. With reference to FIG. 4, binned image 450a is deformed to the target image (which was reconstructed based on the PET scout scan data) by applying elastic motion correction which uses the target image as a target. Elastic motion correction at S260 may utilize mass-preserving optical flow algorithms as is known in the art.

Next, at S270, an image is generated based on the target image and the plurality of motion-corrected images. As illustrated in FIG. 1, the target image and the plurality of motion-corrected images may simply be summed by combination component 160 to generate a high-resolution image, because the motion-corrected images are substantially registered with the target image.

As mentioned above, the manner in which CT data 110 and PET data 120 are acquired (i.e., substantially free of respiratory motion) may result in these data sets being substantially registered with one another. Accordingly, CT data 110 may also be aligned with the image output by component 160, either with or without a refinement step which may include image-based deformable alignment and thus eliminate minor position differences between separate breath holds.

By virtue of this alignment, attenuation correction component 170 may use CT data 110 to perform attenuation correction on the image output by component 160. For example, component 170 may derive a Mu map (e.g., attenuation coefficient map) from CT data 110 as is known in the art. According to some embodiments, the Mu map is derived from a magnetic resonance imaging (MRI) breath hold scan tht is performed as an alternative to the CT scan at S210. Component 170 then uses the Mu map to perform attenuation correction on the image output by component 160, resulting in attenuation-corrected image 180.

According to some embodiments, attenuation-corrected image 180 exhibits a resolution similar to a conventional PET image because it includes all events represented in the second nuclear imaging scan data 130 (as well as events of scan data 120), includes minimal motion artifacts due to the bin-based deformation to the target image, particularly in the region scanned during breath-hold, and is suitably attenuation-corrected due to the availability of inherently-registered CT data 110.

In some embodiments, the first nuclear imaging scan data may be acquired prior to the CT data for quality assurance purposes. For example, an initial PET scout scan may be used to determine whether the patient has been moving excessively or failed to fast, causing unwanted absorption of the radiopharmaceutical. If so, the imaging process may be aborted so as not to subject the patient to unnecessary additional scans. A full-body PET scout scan, optionally together with anatomical information from the CT scan, could be used to detect that the specified dose is correct, whether there is extravasation, or for detecting glycemia.

Each functional component described herein may be implemented at least in part in computer hardware, in program code and/or in one or more computing systems executing such program code as is known in the art. Such a computing system may include one or more processing units which execute processor-executable program code stored in a memory system.

Figure 6:
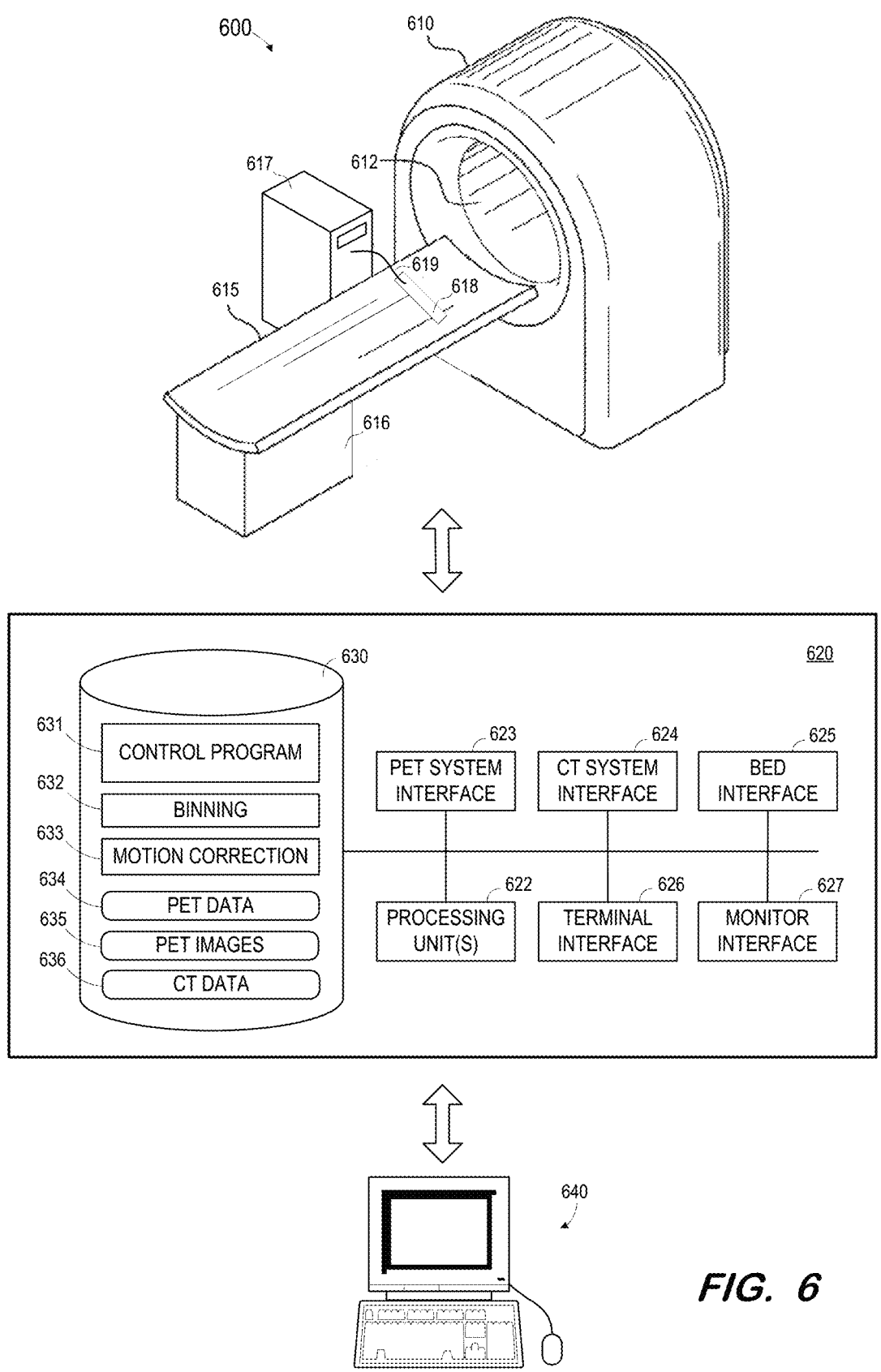
FIG. 6 illustrates an imaging system according to some embodiments.

FIG. 6 illustrates PET/CT system 600 to execute one or more of the processes described herein. Embodiments are not limited to system 600.

System 600 includes gantry 610 defining bore 612. As is known in the art, gantry 610 houses PET imaging components for acquiring PET image data and CT imaging components for acquiring CT image data. The PET imaging components may include any number of gamma cameras in any configuration as is known in the art. The CT imaging components may include one or more x-ray tubes and one or more corresponding x-ray detectors.

Bed 615 and base 616 are operable to move a patient lying on bed 615 into and out of bore 612. In some embodiments, bed 615 is configured to translate over base 616 and, in other embodiments, base 616 is movable along with or alternatively from bed 615.

Movement of a patient into and out of bore 612 may allow scanning of the patient using the CT imaging elements and PET imaging elements of gantry 610. Such scanning may proceed based on scanning parameters such as scan ranges and corresponding scanning speeds. Bed 615 and base 616 may provide continuous bed motion, as opposed to step-and-shoot motion, during such scanning according to some embodiments.

Motion monitor 617 may comprise a respiratory monitor coupled to monitor attachment 618 via cable 619. Monitor attachment 618 may be attached to a patient as is known in the art to acquire a respiratory signal representing phases of motion during nuclear image scanning. The signal may be used as described above to separate acquired PET data into bins representing respective phases of motion.

Control system 620 may comprise any general-purpose or dedicated computing system. Accordingly, control system 620 includes one or more processing units 622 configured to execute processor-executable program code to cause system 620 to operate as described herein, and storage device 630 for storing the program code. Storage device 630 may comprise one or more fixed disks, solid-state random-access memory, and/or removable media (e.g., a thumb drive) mounted in a corresponding interface (e.g., a USB port).

Storage device 630 stores program code of control program 631. One or more processing units 622 may execute control program 631 to, in conjunction with PET system interface 623, bed interface 625, and monitor interface 627, control hardware elements to move a patient into bore 612 and, during the movement, control gamma cameras to rotate around bore 612 and to acquire two-dimensional emission data and motion data of a body located in bore 612 at defined imaging positions during the rotation. The acquired emission data may be stored in memory 630 as PET data 634.

One or more processing units 622 may also execute control program 631 to, in conjunction with CT system interface 624, cause a radiation source within gantry 610 to emit radiation toward a body within bore 612 from different projection angles, and to control a corresponding detector to acquire two-dimensional CT data. The CT data may be acquired substantially contemporaneously with the PET data as described above, and may be stored as CT data 636.

Binning program 632 may be executed to bin acquired PET data as described above. The binned PET data may be reconstructed and stored as PET images 635, and motion correction program 633 may be executed to subject the binned PET images to motion correction based on a target PET image. Binning, motion correction, image combination and attenuation correction may be executed by any combination of control program 631 and other programs.

The output PET image and any intermediate PET and CT images may be transmitted to terminal 640 via terminal interface 626. Terminal 640 may comprise a display device and an input device coupled to system 620. Terminal 640 may display PET scout images, CT images, PET images acquired based on scanning ranges and scanning speeds determined as described herein, uptake volumes, uptake volume classifications, and/or any other suitable images or data. Terminal 640 may receive user input for controlling display of the data, operation of system 600, and/or the processing described herein. In some embodiments, terminal 640 is a separate computing device such as, but not limited to, a desktop computer, a laptop computer, a tablet computer, and a smartphone.

Each of component of system 600 may include other elements which are necessary for the operation thereof, as well as additional elements for providing functions other than those described herein.

Those in the art will appreciate that various adaptations and modifications of the above-described embodiments can be configured without departing from the claims. Therefore, it is to be understood that the claims may be practiced other than as specifically described herein.

What is claimed is:

1. A system comprising:
    a nuclear imaging scanner to:
        execute a first nuclear imaging scan to acquire first nuclear imaging scan data of a body; and
        execute a second nuclear imaging scan to acquire second nuclear imaging scan data of the body; and
    a processing system to:
        generate a target image based on the first nuclear imaging scan data;
        associate each of a plurality of portions of the second nuclear imaging scan data with a respective one of a plurality of motion phases of the body;

for each of the plurality of motion phases of the body, generate a binned image based on the portion of the second nuclear imaging scan data associated with the motion phase;
perform elastic motion-correction on each of the plurality of binned images with the target image as a target of the elastic motion-correction to generate a plurality of motion-corrected binned images; and
generate an image based on the target image and the plurality of motion-corrected binned images.

2. A system according to claim 1, further comprising:
a computed tomography scanner to acquire computed tomography scan data of the body,
the processing system further to attenuation-correct the image based on computed tomography scan data.

3. A system according to claim 2, wherein the computed tomography scan data is acquired while the body is in a breath-hold position, and
wherein at least a portion of the first nuclear imaging scan data is acquired while the body is in the breath-hold position.

4. A system according to claim 1, wherein at least a portion of the first nuclear imaging scan data is acquired while the body is in a breath-hold position, and wherein the second nuclear imaging scan is acquired during free breathing of the body.

5. A system according to claim 4, further comprising a respiratory monitor to receive signals indicating occurrences of each of a plurality of phases of respiration of the body over time,
wherein association of each of the plurality of portions of the second nuclear imaging scan data with one of the plurality of motion phases of the body comprises association of each of the portions of the second nuclear imaging scan data with a respective one of the plurality of phases of respiration.

6. A system according to claim 4, wherein generation of the image comprises summing the target image and the plurality of motion-corrected binned images.

7. A system according to claim 2, wherein the computed tomography scan data is acquired after the first nuclear imaging scan data, and the processing system further to:
determine, based on uptake values of the target image, whether or not to acquire the computed tomography scan data.

8. A method comprising:
acquiring first nuclear imaging scan data of a body;
generating a target image based on the first nuclear imaging scan data;
acquiring second nuclear imaging scan data of the body;
associating each of a plurality of portions of the second nuclear imaging scan data with a respective one of a plurality of motion phases of the body;
generating, for each of the plurality of motion phases of the body, a binned image based on the portion of the second nuclear imaging scan data associated with the motion phase;
deforming each of the plurality of binned images to the target image to generate a plurality of deformed binned images; and
generating an image based on the target image and the plurality of deformed binned images.

9. A method according to claim 8, further comprising:
acquiring computed tomography scan data of the body;
determining an attenuation profile of the body based on the acquired computed tomography scan data; and
correcting the image based on the attenuation profile.

10. A method according to claim 9, wherein the computed tomography scan data represents the body is in a breath-hold position, and
wherein the first nuclear imaging scan data represents at least a portion of the body in the breath-hold position.

11. A method according to claim 8, wherein the first nuclear imaging scan data represents at least a portion, and wherein the second nuclear imaging scan represents free breathing positions of the body.

12. A method according to claim 11, further comprising receiving signals indicating occurrences of each of a plurality of phases of respiration of the body over time,
wherein associating of respective portions of the second nuclear imaging scan data with one of the plurality of motion phases of the body comprises associating of each of the portions of the second nuclear imaging scan data with a respective one of the plurality of phases of respiration.

13. A method according to claim 11, wherein generating the image comprises summing the target image and the plurality of deformed binned images.

14. A method according to claim 9, wherein the computed tomography scan data is acquired after the first nuclear imaging scan data, and further comprising:
determining, based on uptake values of the target image, whether or not to acquire the computed tomography scan data.

15. A system comprising:
a positron emission tomography scanner to execute a scout imaging scan to acquire first positron emission tomography data of a body, and to execute a second imaging scan to acquire second positron emission tomography data of a body in list mode, a duration of the scout imaging scan being shorter than a duration of the second imaging scan;
a computed tomography scanner to acquire computed tomography scan data of the body, the computed tomography scan data being substantially registered with the first positron emission tomography data; and
a processing system to:
generate a target image based on the first positron emission tomography data;
associate each of a plurality of portions of the second positron emission tomography data with a respective one of a plurality of motion phases of the body;
for each of the plurality of motion phases of the body, generate a binned image based on the portion of the second positron emission tomography data associated with the motion phase;
deform each of the plurality of binned images to the target image to generate a plurality of deformed binned images;
generate an image based on the target image, the plurality of deformed binned images; and
attenuation-correct the image based on computed tomography scan data.

16. A system according to claim 15, wherein the computed tomography scan data is acquired while the body is in a breath-hold position, and
wherein at least a portion of the first positron emission tomography data is acquired while the body is in the breath-hold position.

17. A system according to claim 15, wherein the first position emission tomography data is acquired while the body is in a breath-hold position, and wherein the second positron emission tomography data is acquired during free breathing of the body.

18. A system according to claim 17, further comprising a respiratory monitor to receive signals indicating occurrences of each of a plurality of phases of respiration of the body over time,
  wherein association of each of the plurality of portions of second positron emission tomography data with one of the plurality of motion phases of the body comprises association of each of the portions of the second positron emission tomography data with a respective one of the plurality of phases of respiration.

19. A system according to claim 18, wherein generation of the image comprises summing the target image and the plurality of deformed binned images.

20. A system according to claim 15, wherein generation of the image comprises summing the target image and the plurality of deformed binned images.

\* \* \* \* \*